(12) United States Patent
Sandholt et al.

(10) Patent No.: US 11,751,777 B2
(45) Date of Patent: Sep. 12, 2023

(54) MEDICAL DEVICE FOR MONITORING A PHYSIOLOGICAL PULMONARY CONDITION OF A USER, A MOUTHPIECE FOR SUCH MEDICAL DEVICE AND METHOD FOR USING SUCH MEDICAL DEVICE

(71) Applicant: SPIROMAGIC APS, Søborg (DK)

(72) Inventors: Jesper Sandholt, Copenhagen (DK); Jørgen Ole Kjær, Birkerød (DK); Martin Bo Hansen, Birkerød (DK)

(73) Assignee: Spiromagic ApS, Søborg (DK)

( * ) Notice: Subject to any disclaimer, the term of this patent is extended or adjusted under 35 U.S.C. 154(b) by 716 days.

(21) Appl. No.: 16/720,233

(22) Filed: Dec. 19, 2019

(65) Prior Publication Data

US 2020/0155034 A1    May 21, 2020

Related U.S. Application Data

(63) Continuation of application No. 15/319,946, filed as application No. PCT/EP2015/063818 on Jun. 19, 2015, now abandoned.

(30) Foreign Application Priority Data

Jun. 20, 2014  (EP) .................................... 14173337
Dec. 15, 2014  (EP) .................................... 14197958

(51) Int. Cl.
*A61B 5/097*        (2006.01)
*A61B 5/00*         (2006.01)
(Continued)

(52) U.S. Cl.
CPC ............ *A61B 5/097* (2013.01); *A61B 5/0022* (2013.01); *A61B 5/087* (2013.01); *A61B 5/7435* (2013.01);
(Continued)

(58) Field of Classification Search
None
See application file for complete search history.

(56) References Cited

U.S. PATENT DOCUMENTS

| | | | |
|---|---|---|---|
| 5,518,002 | A | 5/1996 | Wolf et al. |
| 5,613,497 | A | 3/1997 | DeBush |

(Continued)

FOREIGN PATENT DOCUMENTS

| | | |
|---|---|---|
| CN | 1178477 A | 4/1998 |
| CN | 2 376 865 | 5/2000 |

(Continued)

OTHER PUBLICATIONS

Lund, M. "Elektronik." Ingeniøren, No. 9, Mar. 1, 2013, pp. 3-5 (with machine English translation). (Year: 2013).*

(Continued)

*Primary Examiner* — Meredith Weare
(74) *Attorney, Agent, or Firm* — Nixon & Vanderhye P.C.

(57) ABSTRACT

The present invention relates to a medical device for monitoring a physiological pulmonary condition of a user, comprising at least one mouthpiece, and a transducer housing, the at least one mouthpiece and the transducer housing being separate elements, the at least one mouthpiece being physically attached to the transducer housing, the at least one mouthpiece, when attached to the transducer housing, being capable of passing at least part of a flow of exhaled or inhaled air through the mouthpiece to the transducer housing, wherein a sensor of the transducer housing is capable of measuring one or more characteristics of the flow of exhaled or inhaled air passed to the transducer housing and of providing data of the flow of exhaled air passed to the transducer housing. Also, the present invention relates to a mouthpiece for such medical device and a method and a system for monitoring a physiological pulmonary condition.

16 Claims, 5 Drawing Sheets

(51) Int. Cl.
*A61B 5/087* (2006.01)
*G16H 40/67* (2018.01)
*A61B 5/091* (2006.01)

(52) U.S. Cl.
CPC .............. *G16H 40/67* (2018.01); *A61B 5/091* (2013.01); *A61B 2560/0209* (2013.01); *A61B 2560/0443* (2013.01); *A61B 2562/08* (2013.01)

(56) References Cited

U.S. PATENT DOCUMENTS

| | | |
|---|---|---|
| 6,367,475 B1 | 4/2002 | Kofoed |
| 6,447,459 B1 | 9/2002 | Larom |
| 2002/0073993 A1 | 6/2002 | Weinstein et al. |
| 2005/0245837 A1 | 11/2005 | Pougatchev |
| 2006/0036134 A1 | 2/2006 | Tarassenko |
| 2006/0253045 A1 | 11/2006 | Coifman |
| 2012/0136271 A1 | 5/2012 | Shavit |
| 2014/0350367 A1 | 11/2014 | Subramaniam |
| 2017/0135605 A1 | 5/2017 | Sandholt et al. |
| 2021/0007628 A1* | 1/2021 | Hansen .................. A61B 5/087 |

FOREIGN PATENT DOCUMENTS

| | | |
|---|---|---|
| CN | 102596030 A | 7/2012 |
| JP | 2004-054489 | 2/2004 |
| WO | WO 2014/085682 | 6/2014 |

OTHER PUBLICATIONS

International Search Report and Written Opinion for the ISA for PCT/EP2015/063818 dated Sep. 28, 2015, 12 pages.
Extended European Search Report for 14173337.8 dated Nov. 6, 2014, 10 pages.
Notification of the First Office Action dated Feb. 27, 2019 in Chinese Application No. 201580032981.0, with English translation, 21 pages.

* cited by examiner

MEDICAL DEVICE FOR MONITORING A PHYSIOLOGICAL PULMONARY CONDITION OF A USER, A MOUTHPIECE FOR SUCH MEDICAL DEVICE AND METHOD FOR USING SUCH MEDICAL DEVICE

CROSS REFERENCE TO RELATED APPLICATIONS

This application is a continuation of U.S. application Ser. No. 15/319,946, filed Dec. 19, 2016, which is the U.S. national phase of International Application No. PCT/EP2015/063818 filed Jun. 19, 2015 which designated the U.S. and claims priority to EP Patent Application No. 14173337.8 filed Jun. 20, 2014 and EP Patent Application No. 14197958.3 filed Dec. 15, 2014, the entire contents of each of which are hereby incorporated by reference.

FIELD OF THE INVENTION

The present invention relates to a medical device for measuring and possibly recording the physiological pulmonary condition of a user of the medical device. The device comprises at least one mouthpiece and a transducer housing, wherein the mouthpiece is intended for the user to blow exhaled pulmonary air into or to draw inhaled air into. The invention also relates to a method and a system for monitoring a physiological pulmonary condition of a user of the medical device. The invention also relates to a mouthpiece for such device and such method.

BACKGROUND ART

Persons suffering from a pulmonary disorder such as asthmatics or COPD (Chronic Obstructive Pulmonary Disease) may need medical attendance at a regular basis. The procedure is often that the person consults a private doctor or a hospital to get diagnosed and that a doctor or other specialist measures and possibly records the physiological pulmonary condition of the person. Such procedure is time-consuming, not only for the person, but also for the doctor or specialist.

Because the procedure is time-consuming, there is a risk that the physiological pulmonary condition of the patient is not measured at a regular basis, which may lead to irreparable deterioration of the physiological pulmonary condition of the person. Hence, there is a need for ensuring that the pulmonary condition of the person is measured regularly to possibly avoid irreparable damage.

US 2002/073993 discloses a pressure monitoring port adapted to be connected to standard flexible tubing for connection to a pressure-monitoring device, such as an aneroid gauge. US2002/073993 neither discloses the aneroid gauge, nor discloses a transducer. The problem to be solved is to assist a patient in coughing to thereby assist in the mobilisation and clearance of secretions. The pressure-monitoring device is connected with the mouthpiece along a hose (not illustrated)

SUMMARY OF THE INVENTION

It is an object of the present invention to wholly or partly overcome the above disadvantages and drawbacks of the prior art. More specifically, it is an object to provide an improved device, which provides an increased possibility of monitoring the physiological pulmonary condition of the user.

It is also an object of the invention to provide a device which provides a possibility of various users using the same transducer of the device, however, preferably not at the same time.

It is even an object of the invention to provide a device which increases the general well-being of the user using the device, if the user uses the device over a prolonged period of time.

The above objects, together with numerous other objects, advantages, and features, which will become evident from the below description, are accomplished by a solution in accordance with the present invention comprising a medical device for monitoring a physiological pulmonary condition of a user, comprising:

at least one mouthpiece, and
a transducer housing, the at least one mouthpiece and the transducer housing being separate elements, the at least one mouthpiece being physically attached to the transducer housing, the at least one mouthpiece, when attached to the transducer housing, being capable of passing at least part of a flow of exhaled or inhaled air through the mouthpiece to the transducer housing, wherein a sensor of the transducer housing is capable of measuring one or more characteristics of the flow of exhaled air or inhaled air passed to the transducer housing and of providing data of the flow of exhaled air or inhaled air passed to the transducer housing.

The at least one mouthpiece, when attached to the transducer housing, may have a flow channel being capable of passing at least part of a flow of exhaled or inhaled air through the mouthpiece to the transducer housing.

The at least one mouthpiece and the transducer being separate devices provides the possibility of using the one and same transducer for different mouthpieces, either mouthpieces being different depending on the user of the mouthpiece, or the mouthpieces being different depending on the pulmonary condition of the user. Users having a poorer pulmonary condition than other users may need a mouthpiece, where the pressure drop is smaller, when blowing into the mouthpiece, than other mouthpieces for users having a better pulmonary condition. Therefore, the mouthpiece and the transducer are not uniquely linked, even if different mouthpieces are used with the one and same transducer. However, the different mouthpieces are not to be used at the same time together with the transducer.

The mouthpiece will be used only for passing flow of exhaled air or inhaled air to the transducer, not for measuring characteristics of the flow of exhaled air blown, or inhaled air drawn, by the user into the mouthpiece. The mouthpiece and the transducer constitute interrelated elements that complement each other and work together. The mouthpiece itself is not capable of monitoring a physiological pulmonary condition of a user, meaning that the mouthpiece only works when used together with the transducer, and vice versa. Also, the transducer itself is not capable of monitoring a physiological pulmonary condition of a user, meaning that the transducer itself only works when used together with the mouthpiece.

Moreover, the at least one mouthpiece and the transducer housing, when being physically attached to each other, may together constitute a hand-held medical device.

Said medical device may have dimensions not exceeding 200 mm along a first extension, 100 mm along a second extension perpendicular to the first extension, and 30 mm along a third extension perpendicular to the first extension and to the second extension.

According to a preferred embodiment of a device according to the invention, the at least one mouthpiece may be void of electronic elements exposed to the interior of the flow channel, such as the at least one mouthpiece being void of electronic elements for measuring characteristics of the flow of exhaled air or inhaled air passed to the transducer housing.

When the mouthpiece is void of electronic elements exposed to the interior of the flow channel, and therefore exposed to a surface of the mouthpiece, such as electronic elements for measuring characteristics of the flow of exhaled air or inhaled air passed to the transducer, the mouthpiece is capable of being cleaned, even in a dishwasher, without the risk of such electronic elements being destroyed during cleaning of the mouthpiece. Regular cleaning of the mouthpiece increases the general well-being of the user and provides a possibility of different users using the same mouthpiece, however, not at the same time.

According to a possible embodiment of a device according to the invention, the mouthpiece may be provided with a flow channel having a first orifice and a second orifice, the first orifice being intended for a user to blow exhaled air or to draw inhaled air into the mouthpiece, and the second orifice being intended for discharge from the mouthpiece or intake of the exhaled air or inhaled air.

The mouthpiece may comprise a restriction or an obstruction configured to create a pressure drop.

Further, the restrictions or obstructions may be a decreasing cross-sectional area of the flow channel, the restriction or obstruction is the cross-sectional area at the second orifice being smaller than cross-sectional area at the first orifice.

Moreover, the mouthpiece having the flow channel may have a cross-sectional area which area at the first orifice may be larger or smaller than the area at the second orifice.

The medical device as described above may comprise several mouthpieces, and the transducer housing may comprise means for registering, such as a detector, configured to detect which of the mouthpieces is attached to the transducer housing.

Also, the restriction or obstruction of one mouthpiece may be smaller than another of the several mouthpieces.

Furthermore, the mouthpiece may also be provided with an air passage having a first orifice and a second orifice, the first orifice being fluidly connected with the flow channel and the second orifice being fluidly connected with a measuring means, which may be a sensor, of the transducer, said air passage being capable of passing at least part of the flow of exhaled air or inhaled air from the flow channel to the transducer housing.

Also, the mouthpiece may be provided with an air passage having an inlet and an outlet, the inlet being fluidly connected with the flow channel and the outlet being fluidly connected with a sensor of the transducer housing, said air passage being capable of passing at least part of the exhaled air or inhaled air from the flow channel to the sensor of the transducer housing.

The flow channel may be provided with at least one of a selected dimension and a selected geometrical shape and a selected size, preferably having a selected cross-sectional area, dimensioned based upon the physiological pulmonary condition of the user.

The flow channel may be provided with a flow restriction/obstruction in the flow channel, said flow restriction/obstruction being dimensioned dependent of the physiological pulmonary condition of the patient. The air passage may be provided with a cross-sectional area dimensioned independently of the physiological pulmonary condition of the patient.

The mouthpiece, when provided with a flow channel and an air passage, may provide a mouthpiece where the flow channel may be dimensioned depending on the pulmonary condition of the user of the device, and where the air passage is only for passing at least part of the flow of exhaled air or inhaled air to the transducer, independently of the user of the device. The air passage does not have any effect related to the pulmonary condition of the user, and the air passage needs no user-dependent calibration or user-dependent dimensioning.

In a preferred embodiment, the flow restriction is a selected size of a cross-sectional area of the flow channel. In possible alternative embodiments, the flow restriction is provided by a selected length of the flow channel for providing a pressure drop along the flow channel of the mouthpiece between a first orifice, where exhaled air enters the flow channel or inhaled air leaves the flow channel, and a second orifice, where exhaled air leaves the flow channel or inhaled air enters the flow channel.

Other means for providing a pressure drop along the flow channel of the mouthpiece between the first orifice and the second orifice may be provided as an alternative to, or in addition to, a certain size of the cross-sectional area and/or certain length of the flow channel for providing a pressure drop.

Other means for providing a pressure drop may be a spiral shaped flow channel having a curve of progression in two dimensions or in three dimensions of a Cartesian coordinate system. A cross-sectional area of a spiral shaped flow channel may either be constant along the line of progression or may change along the line of progression. Alternatively, or additionally, flow obstructions like an impeller or a venturi may be provided in the flow channel.

Geometrical shape of the flow channel may be selected depending on the design of the mouthpiece as such and of the medical device. The cross-section of the flow channel may be circular, oval, polygonal or a combination of these geometries.

Dimensions and geometrical shape of the flow channel may be provided already when manufacturing the mouthpiece, or may be provided as an add-in element to be placed in the mouthpiece as such, prior to use of the mouthpiece.

The mouthpiece may have a first position in relation to the transducer housing, in which first position the first orifice of the mouthpiece is at least partly blocked for exhalation or inhalation of air by a user through the mouthpiece to the transducer housing, the mouthpiece having a second position in relation to the transducer, in which second position the first orifice of the mouthpiece is fully open for exhalation or inhalation of air by a user through the mouthpiece to the transducer, and wherein said mouthpiece is attached to the transducer in both the first position and the second position, so that the mouthpiece and the transducer constitute a single unit, both when in use for monitoring a physiological pulmonary condition of a user and when not in use.

Moreover, the mouthpiece may have a first position in relation to the transducer housing, in which first position the air passage is at least partly blocked for air to pass from the mouthpiece to the transducer housing, the mouthpiece having a second position in relation to the transducer housing, in which second position the air passage is fully open for air to pass from the mouthpiece to the transducer housing, and wherein said mouthpiece is attached to the transducer housing in both the first position and the second position, so that the mouthpiece and the transducer housing constitute a single unit, both when in use for monitoring a physiological pulmonary condition of a user and when not in such use.

According to an embodiment of a device according to the invention, the mouthpiece may have
- a first status in relation to the attachment to the transducer housing, in which first status measuring the flow of exhaled air or inhaled air passed to the sensor of the transducer housing is disabled, and
- a second status in relation to the attachment to the transducer housing, in which second status measuring the flow of exhaled air or inhaled air passed to the sensor of the transducer housing is enabled.

Providing a first status and a second status of the mouthpiece in relation to the transducer housing may be used for saving electrical power from e.g. batteries of the transducer housing, so that electrical power is only provided and only used when measuring is enabled.

According to an embodiment of a device according to the invention, the first status may be a retracted position of the mouthpiece in relation to the transducer housing, and the second status may be an extended position of the mouthpiece in relation to the transducer housing.

Also, in the retracted position, blowing of exhaled air or inhaled air through the mouthpiece is disabled, and in the extended position blowing of exhaled air or inhaled air through the mouthpiece is enabled.

It is easy for the user to provide and ensure a first status disabling blowing through the mouthpiece and excluding electrical power from e.g. batteries of the transducer, which first status is dependent on whether the mouthpiece is in a state enabling blowing through the mouthpiece, or not.

According to an embodiment of a device according to the invention, the mouthpiece may be attached to the transducer housing via a pivot joint having a pivot axis, so that the mouthpiece is capable of pivoting in relation to the transducer, the mouthpiece in a first pivoted position being in the retracted position in relation to the transducer housing, and the mouthpiece in a second pivoted position being in the extended position in relation to the transducer housing.

A pivot joint is an easy and safe method of attaching the mouthpiece to the transducer, while at the same time providing a good possibility for the mouthpiece to be displaced from a first status to a second status, and vice versa.

According to a possible embodiment of a device according to the invention, the air passage may extend along and parallel with the pivot axis of the pivot joint.

When the air passage extends along and parallel with the pivot axis, passing of flow of exhaled air or inhaled air from the flow channel to the transducer can be obtained in any angularly pivoted position of the mouthpiece in relation to the transducer.

Also, the pivot axis of the pivot joint may extend perpendicularly to a main flow direction of the exhaled or inhaled air through the mouthpiece, and the air passage may also extend perpendicularly to a main flow direction of the exhaled or inhaled air through the mouthpiece.

According to a possible embodiment of a device according to the invention, the pivot joint may be constituted by a sealing element with at least part of an outer circumference of the sealing constituting a bearing between the mouthpiece and the transducer housing, and the pivot joint may have a through-hole through the sealing element, delimiting an inner circumference of the sealing element, and constituting the air passage.

Moreover, the sealing element may be at least partly made of elastomer or natural rubber.

A spring may be provided for applying a force to the mouthpiece, maintaining the mouthpiece in the retracted position, said force to be overcome when displacing the mouthpiece from the retracted position to the extended position.

A sealing may function both as pivot joint and as air passage for passing flow of exhaled air or inhaled air from the flow channel to the transducer. Thereby, the one and same element, that is the sealing, provides two different functions necessary for the function of the embodiment of the device.

According to an embodiment of a device according to the invention, the device may comprise the mouthpiece being a first mouthpiece, a second mouthpiece and the transducer housing, the first mouthpiece having a flow channel with a first cross-sectional area restriction and the second mouthpiece having a flow channel with a second cross-sectional area restriction, the first and the second cross-sectional areas at the restrictions being viewed perpendicularly to a longitudinal axis along a main flow direction of the flow channels, and wherein the second cross-sectional area may be smaller than the first cross-sectional area.

Providing at least two different mouthpieces, with different cross-sectional areas at cross-sectional area restrictions of the flow channel, makes it possible, either for the user to switch between the one or the other mouthpiece, or for the doctor or other specialist to provide to the one or the other user the first or the second mouthpiece, depending on the pulmonary condition of the user, and without having to consider which transducer to use, because the transducer functions with either one of the at least two mouthpieces.

The medical device may be configured to attach to a first mouthpiece, a second mouthpiece or a third mouthpiece. The user can use one of the first, the second and the third mouthpiece at a time.

The restriction of the first mouthpiece may be smaller than the restriction of the second and third mouthpieces.

The restriction of the second mouthpiece may be smaller the restriction of the third mouthpiece.

The first mouthpiece may be configured to measure at a first flow rate interval, the second mouthpiece may be configured to measure at a second flow rate interval, and the third mouthpiece may be configured to measure at a third flow rate interval.

The transducer housing may comprise a means for registering, such as a detector, configured to detect the mouthpiece when attached to the transducer housing.

The means for registering is configured to detect which of the first and second mouthpieces are attached to the transducer housing. The detection may be mechanical or electronic.

The means for registering may be a tag detector configured to detect a tag of the mouthpiece. In this way, the transducer is able to detect which of the first, second or third mouthpiece is attached to the transducer housing and thus the measuring of the inhaled or exhaled air is calibrated accordingly. The tag may be an RFID tag.

The detector may also be a mechanical detector configured to detect e.g. a geometrical dimension of a mouthpiece for identification of the mouthpiece.

According to a possible embodiment of a device according to the invention, a transmitter of the transducer housing may be capable of transmitting the data of the flow of exhaled air or inhaled air passed to the transducer housing further on to a remote data receiver, said data being correlated with a user of the medical device, and the remote data receiver being located by at least one of the following recipients of the data: a hospital medicating the patient, a doctor of the patient, a relative of the patient, the patient himself or herself.

Remote monitoring of the user at different locations, either at one location or the other location, or at different locations at the same time, such as both at the specialist and at relatives of the user, provides enhanced possibilities of assisting the user in remembering to perform regular measurements of the pulmonary condition and/or of detecting a deterioration or improvement of the pulmonary condition of the user.

According to a possible embodiment of a device according to the invention, the remote data receiver may be at least one of the following data receivers: a mobile phone or cellular phone, a watch or other wearable, a tablet, a laptop.

The remote data receiver being a non-stationary device increases the possibility of the user herself or himself, a relative to the user or the doctor or other specialist being capable of monitoring that the user performs regular measurements by using the device and possibly recording the measurements performed by the user.

According to a possible embodiment of a device according to the invention, outer boundaries of the at least one mouthpiece, in the retracted position, may be enclosed within outer boundaries of the transducer housing, so that when the mouthpiece is attached to the transducer housing, and when the mouthpiece is in the retracted position, outer boundaries of the device are outer boundaries of the transducer.

When the device is not in use by the user, it is an advantage that the device does not take up more space than necessary. When not in use, the mouthpiece is not needed, and it is an advantage that the mouthpiece is wholly embedded in the transducer.

Objects of the invention are also accomplished by a method for monitoring a physiological pulmonary condition of a user of a medical device according to the present invention, said method comprising the steps of:
- displacing the mouthpiece from a retracted position to an extended position for measuring a flow of air exhaled or inhaled air by the user and blown or drawn into the mouthpiece,
- the user blowing air into a first orifice or drawing air into a second orifice of the mouthpiece, through a flow channel of the mouthpiece and through a second orifice or first orifice, respectively, of the mouthpiece,
- passing at least part of the flow of air from the flow channel of the mouthpiece to an air passage between the mouthpiece and the transducer housing,
- passing the flow of exhaled air or inhaled air from the air passage to a sensor of the transducer housing for measuring characteristics such as air pressure of the flow or air, and
- displaying data related to the characteristics of the flow of exhaled air or inhaled air, said data being displayed on the transducer and/or on a remote data receiver.

The method described above for monitoring a physiological pulmonary condition of a user of a medical device according to the present invention may comprise the further steps of:
- measuring and recording, by the transducer housing and/or by a remote data receiver, first data of a first exhalation or inhalation and blowing of air or drawing of air into the mouthpiece,
- measuring and recording, by the transducer housing and/or by a remote data receiver, second data of a second exhalation or inhalation and blowing of air or drawing of air into the mouthpiece,
- said first data and said second data being measured and recorded with a time interval between measuring the first data and the second data,
- measuring a possible change of data between the first data and the second data so as to establish any difference between the first data and the second data, and
- using a possible change between the first data and the second data to establish whether the physiological pulmonary condition of the user is deteriorating or improving.

Moreover, the mouthpiece may comprise a flow channel for a user to blow exhaled air into or to draw inhaled air into, said mouthpiece being void of electronic elements exposed to an interior of the flow channel, with the proviso that said electronic elements are for measuring characteristics of the flow of exhaled air or inhaled air, and said mouthpiece being provided with at least one air passage for passing of at least part of the flow of exhaled air or inhaled air from the flow channel of the mouthpiece, out of the mouthpiece, and to an exterior transducer for measuring characteristics of the flow of exhaled air or inhaled air.

Objects of the invention are also accomplished by a system for monitoring a physiological pulmonary condition of a user, said system comprising:
- a medical device according to the invention,
- a data transmission channel between the medical device and a remote data receiver,
- a data recording means for recording data received by the remote data receiver,
- the data transmission channel being at least one of the following wireless data transmission channels: WPAN such as Bluetooth, WLAN such as Wi-Fi, WMAN such as WiMAX and mobile/cellular networks, and
- the data recording means being embedded in at least one of the following remote data receivers: a mobile phone or cellular phone, a watch or other wearable, a tablet, a laptop, wherein the data recording means are able to record first data and second data, the second data being different from the first data, and are provided with data displaying means for displaying the first data and the second data.

Transmitting and receiving data via wireless data transmission channels provide a good possibility of monitoring the user's pulmonary condition at different locations, either one location or the other location, or at different locations at the same time, such as both at the specialist and at relatives of the user. Also, by recording at least two sets of data, a trend in the pulmonary condition of the user may be monitored, to see whether the condition gets worse or gets better.

BRIEF DESCRIPTION OF THE DRAWINGS

The invention and its many advantages will be described in more detail below with reference to the accompanying schematic drawings, which for the purpose of illustration show some non-limiting embodiments and in which.

DETAILED DESCRIPTION OF THE INVENTION

Figure 1:
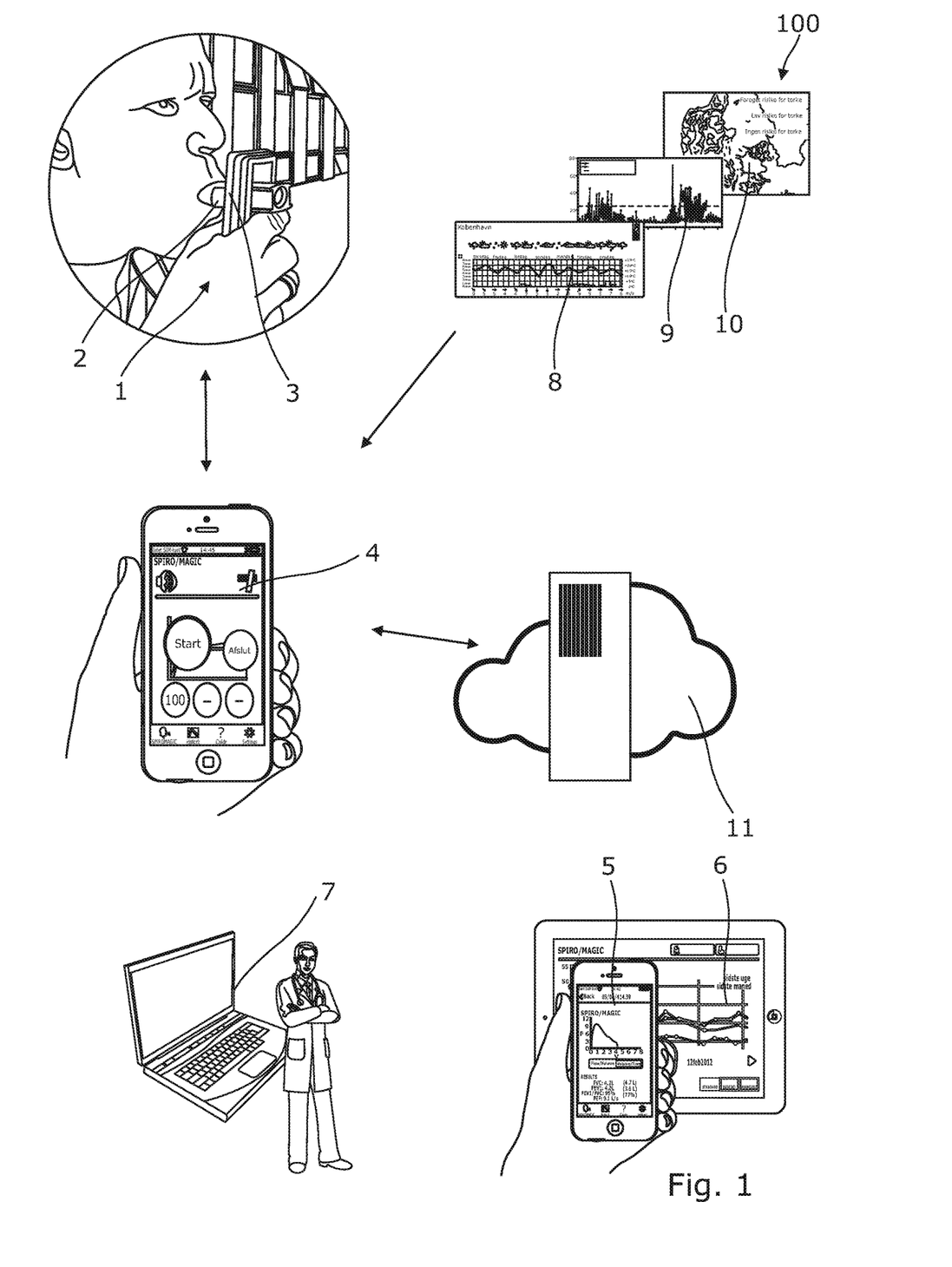
FIG. 1 shows a system according to the invention for monitoring a physiologic pulmonary condition of a user.

FIG. 1 shows a system 100 for monitoring the physiological pulmonary condition of a user. The system comprises a medical device 1 according to the invention. The medical device is to be used by a user exhaling air into a mouthpiece 2 of the medical device 1 or inhaling air through the mouthpiece, creating a flow of exhaled air or inhaled air through the mouthpiece 2. One or more characteristics of at least part of said flow of exhaled air or inhaled air is/are to be measured by a sensor 30, shown in FIG. 4, of a transducer housing 3, also in short called a transducer, of the medical device 1. The sensor of the transducer housing 3, apart from measuring one or more characteristics of at least part of said flow of exhaled air or inhaled air, also constitutes a means for holding the medical device by one hand of the user, while the user exhales air or inhales air into a mouthpiece 2 of the medical device 1.

Figure 4:
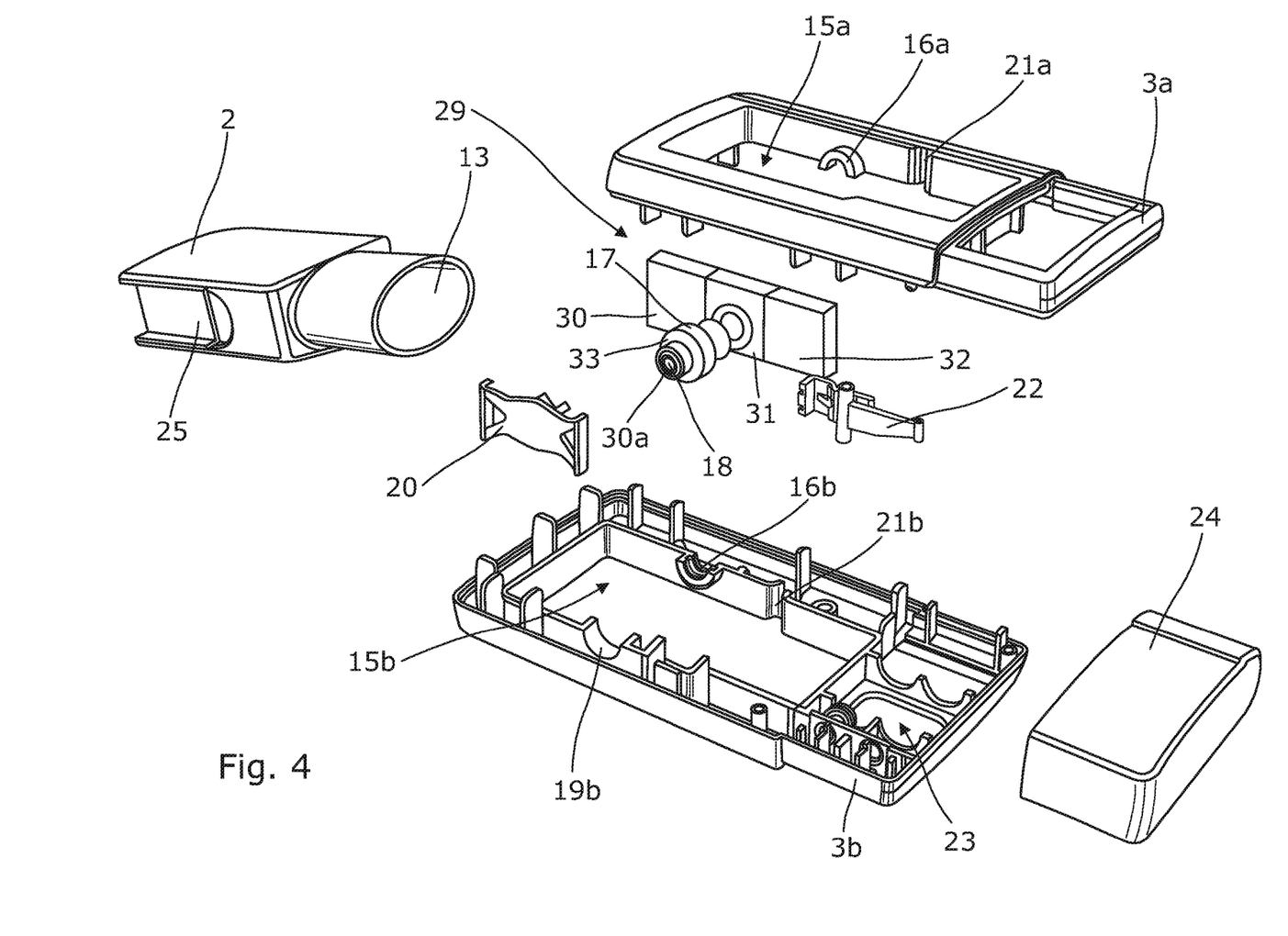
FIG. 4 is a perspective, exploded view of the embodiment of the medical device.

The sensor 30, shown in FIG. 4, measures a pneumatic value of the flow of the air exhaled into the mouthpiece 2, or of the flow of the air inhaled through the mouthpiece 2. The transducer housing 3 may also comprise a transducer 31 and a transmitter 32. The transducer 31 converts a pneumatic signal from the sensor 30 to an electronic signal, providing data of the flow of inhaled air or exhaled air passed to the sensor 30.

If the transducer housing contains a transmitter 32, the transducer 31 converts a signal of the sensor 30 into a signal for the transmitter 32. The transmitter 32 sends the electronic signal of the transducer 31 to a remote data receiver 4 (shown in FIG. 1) when the pneumatic signal from the sensor 30 has been converted to an electronic signal by the transducer 31.

Figure 2:
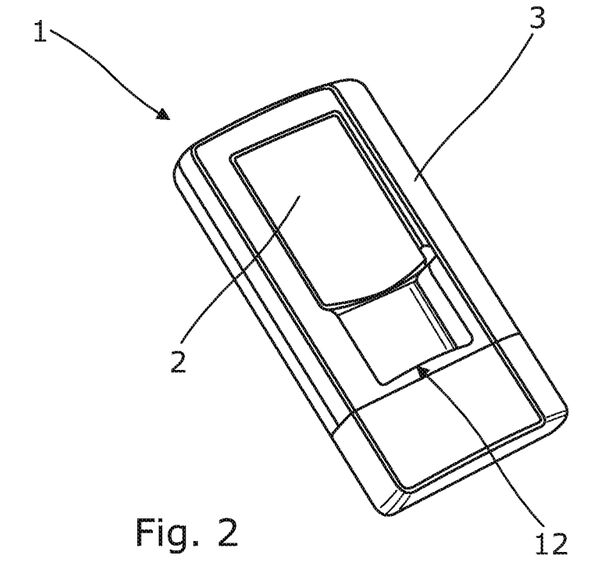
FIG. 2 is a perspective view of an embodiment of the device for measuring a physiologic pulmonary condition of a user, and in which measuring is disabled.

As shown in FIG. 4, the mouthpiece 2 is attached to the transducer housing 3 along a pivot joint 33 having a pivot axis. The pivot joint comprises a pivot bearing 20 and an element 17. The mouthpiece 2 and the transducer housing 3 are capable of being hand-held together by one hand, when the mouthpiece is physically attached to the transducer. The medical device 1 as such, and the function of the medical device 1 as such, is described in more detail with reference to FIGS. 2ff.

The transducer housing 3 is shown as extending all the way around the mouthpiece, but in another embodiment the transducer housing merely extends along one side of the mouthpiece, or along two or three sides. The transducer housing is the unit comprising the sensor and merely functions as a holder of the sensor, transducer, transmitter, batteries, etc.

In another embodiment in which the transducer housing does not extend all the way around the mouthpiece, the pivot joint comprises the element 17 and not the pivot bearing 20 arranged on an opposite side of the mouthpiece.

The system 100 furthermore comprises a range of possible remote data receivers 4 of data transmitted by the transducer 31 in the transducer housing 3 of the medical device 1, the data being related to the one or more characteristics measured by the transducer 31 of the transducer housing 3. The range of possible remote data receivers 4, 5, 6, 7 may comprise: a mobile or cellular phone of the user, a mobile or cellular phone 5 or a tablet 6 of others than the user, such as a doctor or other specialist or a relative of the user, or a laptop 7 or a tablet or a dongle of the user or of others than the user, such as a doctor or other specialists or a relative of the user. The list of remote data receivers is not exhaustive, and other remote data receivers known to the skilled person may be used.

Measurements by the transducer 31 of the transducer housing 3 of one or more characteristics of the flow of exhaled air or inhaled air through the mouthpiece 2 may be correlated with other data. Other data may be one or more of the following data: present and/or future weather conditions 8 in the environment of the user, rate of polluting particles 9 in the environment of the user, rate of pollen 10 in the environment of the user. The list of other data is not exhaustive, and other data relevant to the measurements by the transducer 31 of the transducer housing 3 of one or more characteristics of the flow of exhaled air or inhaled air may be used.

The other data may be data based on measurements performed simultaneously with measurement of the one or more characteristics of the flow of exhaled air or inhaled air. Alternatively or additionally, the data may be based on historic or empiric data at the location where the user is situated, when performing measurements of the exhaled air or inhaled air. Therefore, the transducer housing 3 may comprise means for establishing the position of the medical device 1, and therefore of the user, such as GPS (Global Positioning System).

The system comprises computer programs with algorithms for processing data transmitted by the transducer 31 of the transducer housing 3 to the one or more remote data receivers 4, 5, 6, 7. The computer programs are provided distant from the transducer 31 of the transducer housing 3 and distant from the remote data receivers 4, 5, 6, 7, such as so-called cloud computing 11. If the system comprises such distant computer programs, the transducer housing 3 and/or the remote data receivers 4, 5, 6, 7 comprise telecommunications means for communicating with the distant computer programs. Alternatively or additionally to using distant computer programs, computer programs and algorithms needed for processing the data transmitted by the transducer 31 of the transducer housing 3 are stored at one or more of the remote data receivers 4, 5, 6, 7.

The computer programs, software and algorithms, whether distant to the one or more of the remote data receivers 4, 5, 6, 7 or locally stored on one or more of the remote data receivers 4, 5, 6, 7, may have various features for displaying the measurements of the one or more characteristics of the flow of exhaled air or inhaled air. The measurement may be displayed according to a number being a percentage of the user's pulmonary capacity correlated with a reference pulmonary capacity. Alternatively, the measurement may be displayed as a graph showing the user's pulmonary capacity over a period of time during one exhalation of air or inhalation of air, possibly correlated with a reference pulmonary capacity. Alternatively, the measurement may be displayed as a graph showing the user's pulmonary capacity as a trend over a period of time covering at least two different exhalations of air or two different inhalations of air, possibly correlated with a reference pulmonary capacity. Alternatively, the measurement may be displayed as a graph showing the user's pulmonary capacity over a period of time during one exhalation of air or one inhalation of air, possibly correlated with a reference pulmonary capacity. The reference pulmonary capacity may be a pulmonary capacity of a person not suffering from possible pulmonary incapacity like the user. The reference person is a person having the same gender and/or similar age and/or similar environmental conditions. The reference pulmonary capacity may instead be a pulmonary capacity of the user during one or more earlier measurements of the pulmonary capacity of the user, for displaying a trend.

The remote data receivers, apart from being capable of receiving data from the transducer 31 of the transducer housing 3, may also be capable of processing, displaying, recording and/or storing the data. Depending on the type of remote data receiver, depending on the user of the remote data receiver and depending on the purpose for which the remote data receiver is receiving the data, the remote data receiver may be able to both display, process, record and store the data, or the remote data receiver may be able to only perform some of the operations mentioned.

FIG. 2 shows a medical device 1 for measuring one or more characteristics of a flow of air exhaled or inhaled air by a user. As mentioned, the medical device 1 comprises a mouthpiece 2 and a transducer housing 3. The mouthpiece 2 is attached to the transducer housing 3 via a pivot joint 33 (see FIG. 4). The pivot joint of the mouthpiece 2 is releasable, thereby enabling the mouthpiece 2 to be detached from the transducer housing 3.

Figure 5A:
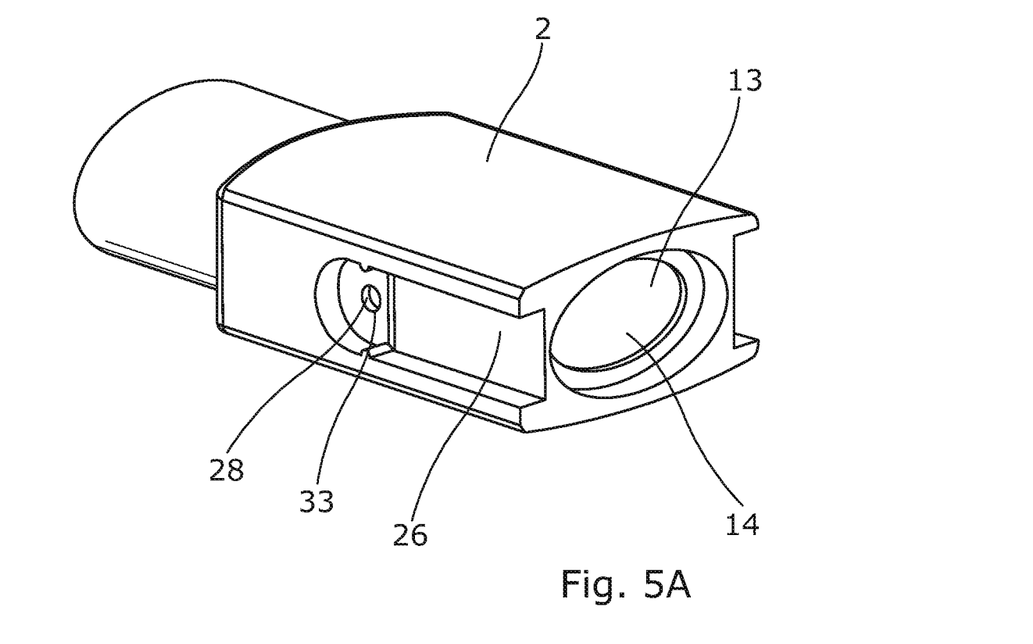
FIGS. 5A and 5B are perspective views of the embodiment of a mouthpiece for a medical device according to the invention.
Figure 5B:
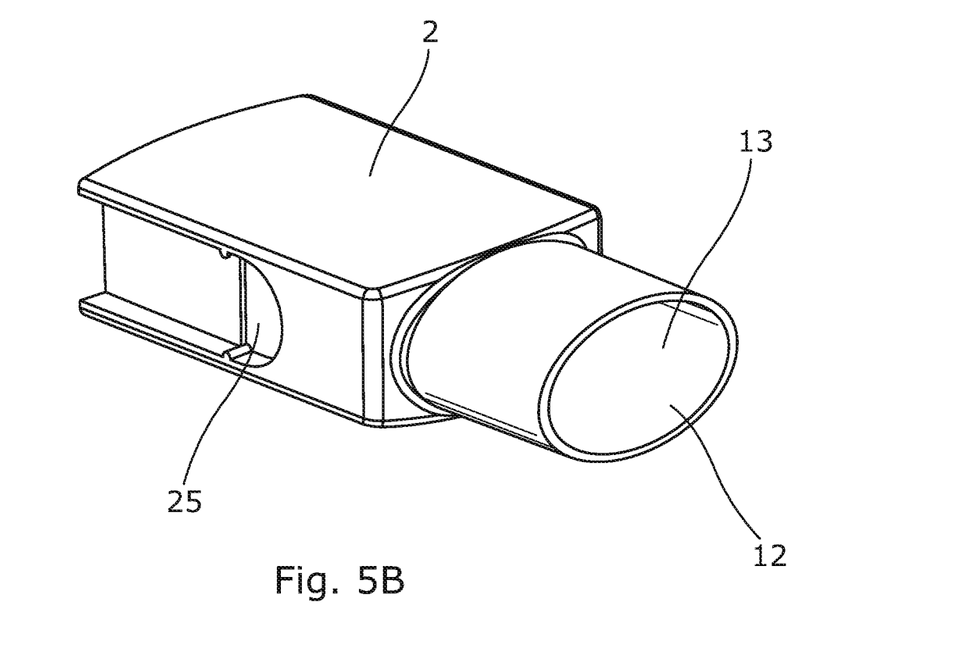

The mouthpiece 2 is provided with a first orifice 12 for a flow channel 13 as shown FIG. 5B. The flow channel 13 is shown in FIGS. 7a-7d, in that FIGS. 7a-7d illustrate partly cross-sectional views in which the mouthpiece is shown in cross-section. As shown in FIG. 5A, the mouthpiece 2 is provided with a second orifice 14 of the flow channel 13. The first orifice 12 is intended for a user to blow exhaled air into or to draw inhaled air out of the mouthpiece 2. The second orifice 14 (see FIG. 5A) is for the flow of exhaled air to leave the mouthpiece 2 or for the flow of yet un-inhaled air to enter the mouthpiece 2. An air passage 18 (see FIG. 4) extends between the flow channel 13 of the mouthpiece 2 and the transducer 31 of the transducer housing 3. The transducer housing 3 is provided with electronics (not shown) for measuring one or more characteristics, such as a pneumatic pressure, of flow of air exhaled or inhaled by the user, blown by the user into the first orifice 12 and flowing through the flow channel 13 of mouthpiece 2. Part of the flow is pressed into the air passage 18, and e.g. the air pressure is measured by the transducer 31 of the transducer housing 3.

Figure 3:
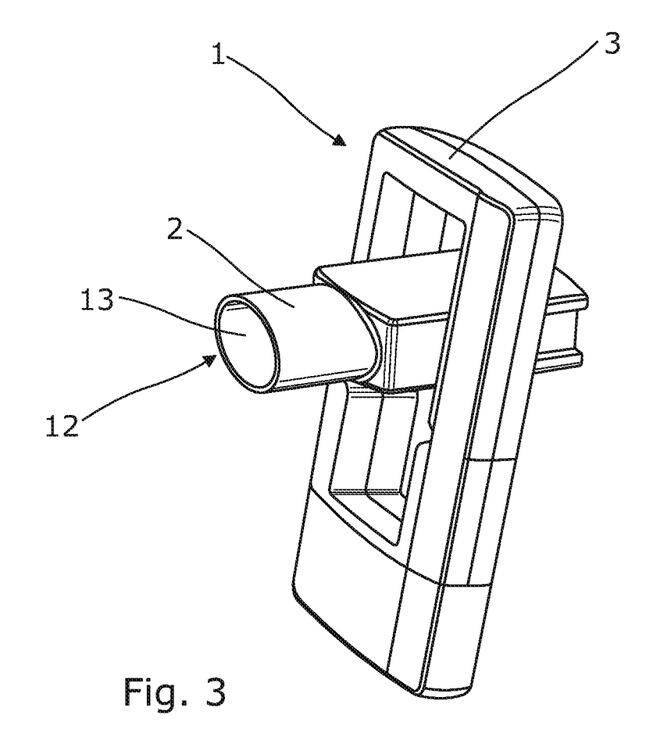
FIG. 3 is a perspective view of the embodiment of a medical device shown in FIG. 2 for measuring a physiologic pulmonary condition of a user, and in which measuring is enabled.

In FIG. 2, the mouthpiece 2 is shown in a first position in which the mouthpiece is aligned with the transducer housing 3, and blowing of exhaled air, or drawing of inhaled air, into and through the flow channel 13 of the mouthpiece 2 is disabled. When the mouthpiece is in its retracted position, the user is not able to blow into the mouthpiece or the air passage is at least partly blocked for air to pass from the mouthpiece to the transducer. In FIG. 3, the mouthpiece 2 is shown in a second position in which the mouthpiece is pivoted in relation to the transducer housing 3 and blowing of exhaled air, or drawing of inhaled air, into and through the flow channel 13 of the mouthpiece 2 is allowed. When the mouthpiece is in its pivoted position, the user is able to blow into the mouthpiece or the air passage is fully open for air to pass from the mouthpiece to the transducer. The first position constitutes a first status of the mouthpiece 2, where the mouthpiece 2 is in a retracted position in relation to the transducer housing 3. When the mouthpiece 2 is in the first, retracted status in relation to the transducer housing 3, measurement by the transducer housing 3 of one or more characteristics of the flow of air is disabled. Electric power from batteries or other source of electrical power is thereby saved, when blowing of exhaled air, or drawing of inhaled air, through the mouthpiece 2 is disabled, and where corresponding measurements of the flow of air are therefore not needed.

In another embodiment, the mouthpiece may be slidably connected with the transducer housing 3, so that the air passage in the second position is fully open and aligned with the sensor 30 and in the first position is closed and unaligned with the sensor.

Furthermore, in the first, retracted status of the mouthpiece 2 in relation to the transducer housing 3, where blowing of exhaled air, or drawing of inhaled air, into and through the flow channel 13 of the mouthpiece 2 is disabled, outer boundaries of the mouthpiece 2 are wholly enclosed within outer boundaries of the transducer housing 3, resulting in the medical device 1 as a whole not taking up more space than the transducer housing 3 itself.

FIG. 3 shows the embodiment of the medical device 1 being the same embodiment as that shown in FIG. 2. As mentioned, the medical device 1 comprises the mouthpiece 2 and the transducer housing 3. The mouthpiece 2 is attached to the transducer housing 3 via a pivot joint 33 (see FIG. 4). The mouthpiece 2 is releasable from the transducer housing in the pivot joint, thereby enabling the mouthpiece 2 to be detached from the transducer housing 3.

In FIG. 3, the mouthpiece 2 is pivoted to a position in relation to the transducer housing 3, in which blowing of exhaled air, or drawing of inhaled air, into and through the flow channel 13 of the mouthpiece 2 is enabled. The position constitutes a second status of the mouthpiece, where the mouthpiece is in an extended position in relation to the transducer housing 3. When the mouthpiece 2 is in the second, extended status in relation to the transducer housing 3, measurement by the transducer 31 of the transducer housing of one or more characteristics of the flow of air is enabled.

The mouthpiece 2 is preferably void of any electronics for measuring, transmitting, receiving or recoding of data related to the flow of exhaled air or inhaled air through the flow channel 13 (shown in FIG. 3) of the mouthpiece 2. Thereby, the mouthpiece 2, when detached from the transducer housing 3, can easily be cleaned by the user, either by hand in tap water or in a dish washer, without the risk of any electronics being damaged during cleaning of the mouthpiece 2. Thereby, the general well-being of the user of the medical device 1 is increased due to the possibility of reducing the risk of bacteria gathering on the mouthpiece 2. Also, by providing a possibility of easy cleaning of the medical device 1, the mouthpiece 2 may be used by different users without the risk of bacteria from one user being passed on to other users.

The transducer housing 3 is provided with electronics and electrical power for measuring one or more characteristics of the flow of exhaled air or inhaled air through flow channel 13 of the mouthpiece 2. The electronics may be one or more pressure sensors, one or more flow sensors or other sensors for measuring characteristics of the flow of exhaled air or inhaled air through the mouthpiece 2. The transducer housing 3 is also provided with means, such as the transmitter 32 (shown in FIG. 4), for transmitting data of the measurements to a remote data receiver. Data is preferably transmitted via wireless data transmission such as Bluetooth. Data is also preferably transmitted to a mobile or cellular phone, which phone has computer programs for processing the data received (see FIG. 1). The mobile or cellular phone may also have hardware and computer programs for passing on data to other remote data receivers, either a remote data receiver at a doctor or other specialist, or a remote data receiver at the user herself or himself or at relatives of the user.

FIG. 4 shows a perspective view of the medical device 1 in an exploded view. The transducer housing 3 is constituted by a first part 3a and a second part 3b to be mutually joined. The first part 3a and the second part 3b of the transducer housing 3 are provided with cavities 15a and 15b for taking up the mouthpiece 2. The cavities 15a, 15b are provided with first recesses 16a, 16b for accommodating a sealing element 17 such as a rubber sealing 17 comprising an air passage 18. The transducer housing 3 is also provided with a second recess 19a, 19b (only the second recess 19b is visible and shown) for accommodating a pivot bearing 20. The first part 3a and the second part 3b of the transducer housing 3 are furthermore provided with third recesses 21a, 21b for accommodating a spring-like element 22 for maintaining the mouthpiece 2 in a retracted position as shown in FIG. 2, when the medical device is not in use. In order to displace the mouthpiece 2 from the first, retracted status shown in FIG. 2, to the second, extended status shown in FIG. 3, a spring force from the element 21 must be overcome. The pivot bearing 20 may also comprise a spring-like element for forcing the mouthpiece against the element 17 and thus the air passage 18.

The transducer housing 3 is also provided with a fourth recess 23 and a cover 24 for the fourth recess 23, for accommodating batteries providing electric power to electronics (not shown) inside the transducer housing 3. The electronics are for measuring one or more characteristics of the flow of exhaled air or inhaled air and for transmitting data of the measured flow of exhaled air or inhaled air to one or more remote data receivers 4, 5, 6, 7 (see FIG. 1) of the data.

The mouthpiece 2 is moulded in one piece provided with slots 25, 26 (slot 26 is shown in FIG. 5A and slot 25 is shown in FIG. 5B) on each side of the mouthpiece 2 for attaching the mouthpiece 2 to the transducer housing 3 by sliding the slots along the one pivot bearing constituted by the sealing element 17, such as the rubber sealing 17, and the pivot bearing 20, opposite the rubber sealing 17. When the mouthpiece 2 has been attached to the transducer housing 3 by means of the rubber sealing 17 and the pivot bearing 20, the air passage 18 provided in the rubber sealing 17 is in line with a corresponding hole 28 (not shown, see FIG. 5A) in the one side of the mouthpiece 2. Thereby, at least part of flow of exhaled air or inhaled air through the flow channel 13 of the mouthpiece 2 is passed to the transducer housing 3 through the air passage 18. In the embodiment shown, the hole 18 of the rubber sealing 17 extends perpendicularly to a longitudinal extension of the mouthpiece 2 and thus extends perpendicularly to a longitudinal extension of a main flow direction of exhaled air or inhaled air through the mouthpiece 2. Accordingly, also the air passage 18 extends perpendicularly to the longitudinal extension of the mouthpiece 2 and thus extends perpendicularly to the longitudinal extension of a main flow direction of exhaled or inhaled air through the mouthpiece 2.

The mouthpiece 2 may be provided with a marking (not shown) at a surface of the mouthpiece 2 for showing the user at which side of the mouthpiece the hole 28 is provided. Alternatively, a hole may be provided in each side of the mouthpiece 2, the one hole communicating with the air passage 18 and the other hole being blocked by the pivot bearing 20. Thereby, the mouthpiece 2 may be attached to the transducer housing 3 without regard to where, that is at which side, a hole to be aligned with the air passage 18 is provided.

FIGS. 5A and 5B show perspective views of the mouthpiece 2 according to the embodiment shown in FIG. 2 and FIG. 3. As mentioned, the mouthpiece 2 has a flow channel 13 with a first orifice 12 for blowing of exhaled or inhaled air by the user through the flow channel 13 and a second orifice 14 for the exhaled or inhaled flow of air to leave or enter the mouthpiece 2. The mouthpiece 2 also has the hole 28, see FIG. 5A, passing at least part of the flow of exhaled air or inhaled air from the flow channel 13 to the transducer housing 3 (see also FIG. 4).

Figure 6:
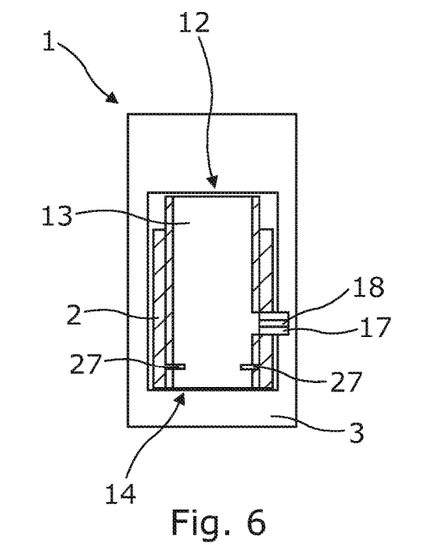
FIG. 6 is a plane, cross-sectional view of the device according to the invention.

FIG. 6 is a schematic view of the medical device 1 shown in FIGS. 2-4. The medical device comprises a mouthpiece 2 and a transducer housing 3. The mouthpiece 2 is detachably attached to the transducer housing 3 via a pivot joint 33 having a pivot bearing 20 (see FIG. 4) at least at one side of the mouthpiece 2, and the sealing element 17, such as the rubber sealing 17 at the other side of the mouthpiece 2.

The sealing element may be a tubular part having a sealing ring arranged either around the tubular part or arranged in the end of the tubular part closest to the sensor. The sealing element or rubber element may thus comprise a sealing ring of rubber or similar sealing material, and the remaining part of the element may be made in another suitable material, such as plastic, composite etc. The air passage 18 extends along and parallel with a longitudinal axis of the tubular part of the sealing element 17.

In FIG. 2, the mouthpiece 2 is in the first status, that is in the retracted position in relation to the transducer housing 3, in which exhaling or inhaling of air through the flow channel 13 between the first orifice 12 and the second orifice 14 is disabled, and measurement of one or more characteristics of a flow of air is therefore disabled, to save battery power or other electrical power for the electronics enclosed in the transducer housing 3.

The air passage 18 extends through the rubber sealing as shown in FIG. 4 from the flow channel 13 of the mouthpiece 2 to the electronics 29 embedded or fastened in the transducer housing 3. The air passage 18 extends along and parallel with a longitudinal axis of the rubber sealing 17, and also functions as pivot bearing at one side of the mouthpiece 2. Thereby, the air passage 18 is capable of passing at least part of the flow of exhaled air or inhaled air from the flow channel 13 to the sensor 30 of the transducer housing 3 in any angularly pivoted position of the mouthpiece 2 in relation to the transducer housing 3, apart from the position shown, where the mouthpiece 2 is in the first, retracted status in relation to the transducer housing 3 due to the fact the user is unable to blow air into or out of the mouthpiece in that position.

Figure 7A:
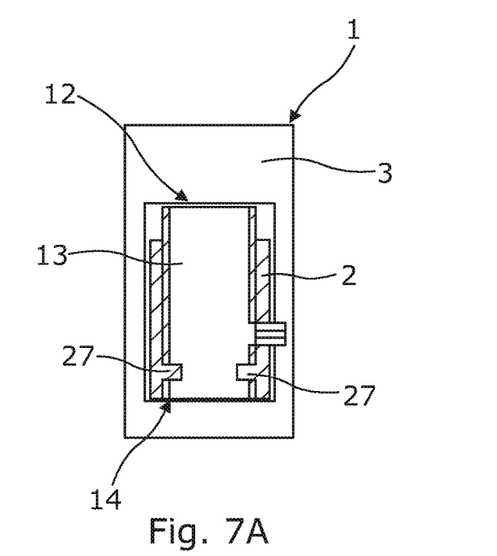
FIGS. 7a-7d are plane cross-sectional views of various embodiments of a mouthpiece for a medical device according to the invention.
Figure 7B:
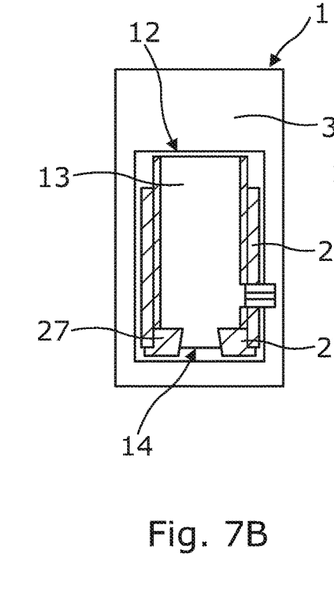
Figure 7C:
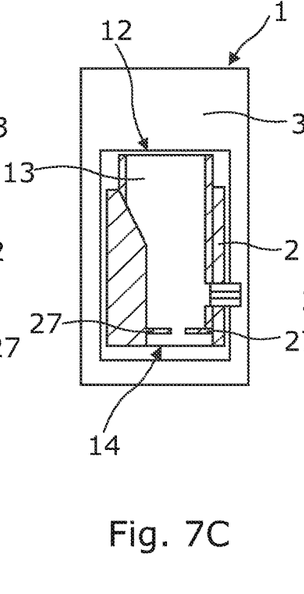
Figure 7D:
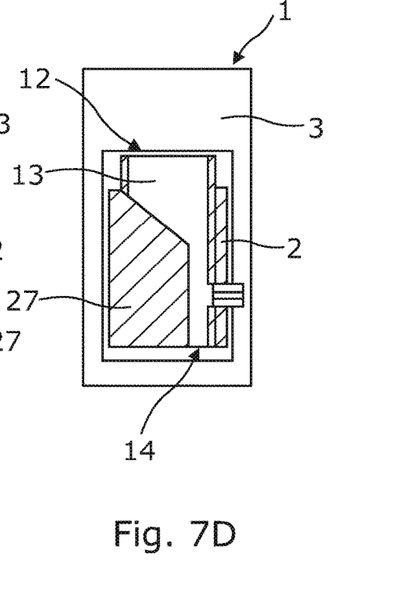

FIGS. 7a-7d show different cross-sections of the flow channel 13 through the mouthpiece 2. The mouthpiece comprises a restriction or obstruction 27 configured to create a pressure drop. The obstruction or restriction is a decreased cross-sectional area of the flow channel, as shown in FIGS. 6-7d. In FIG. 7d, the obstruction/restriction is the cross-sectional area at the second orifice being smaller than cross-sectional area at the first orifice. Different users of a medical device 1 according to the invention have different pulmonary capacities. The cross-sectional area of the flow channel 13 is preferably dimensioned according to the pulmonary capacity of the user. Users having a relatively large or more normal pulmonary capacity are capable of blowing exhaled air, or capable of drawing inhaled air, through a mouthpiece having a larger cross-sectional area than users having a relatively small pulmonary capacity. Users having a relatively small pulmonary capacity may be persons suffering from pulmonary disease or incapacity, or may be children.

If the pulmonary capacity of the user is very small compared to the average human pulmonary capacity, the cross-sectional area of part of the flow channel 13 is small as shown in FIGS. 7c and 7d. If the pulmonary capacity of the user is moderate compared to average human pulmonary capacity, the cross-sectional area of the flow channel 13 is smaller, as shown in FIG. 7b, than the cross-sectional area shown in FIG. 7a. If the pulmonary capacity of the user is similar to average human pulmonary capacity, the cross-sectional area of part of the flow channel 13 is larger, as shown in FIG. 7a, than the cross-sectional area shown in FIG. 7b and as shown in FIGS. 7c and 7d.

In the embodiments shown, the cross-sectional area of the flow channel 13 of the mouthpiece 2 is delimited by different types and shapes of one or more obstructions 27 provided in the flow channel 13. The one or more restrictions/obstructions 27 provided may extend from an inner side wall in itself extending longitudinally straight along the flow channel 13 through the mouthpiece 2. Alternatively, or additionally, the one or more restrictions/obstructions may be a change of the longitudinal extension of the sidewall itself of the flow channel 13 through the mouthpiece 2.

Common to the different mouthpieces 2 with different cross-sectional areas of the flow channel 13 between the first orifice 12 and the second orifice 14, as shown in FIGS. 7a-7d, is that each of the different mouthpieces 2 (a first, a second or third mouthpiece) may be used in the one and same transducer housing 3. Therefore, the medical device 1 only has to be calibrated for the specific user by selecting the one or the other mouthpiece 2. The transducer housing 3 may have a means for registering 30a whether it is the one or the other mouthpiece 2 with the one or the other cross-sectional area of the flow channel 13, which is attached to the transducer housing 3. Thus, the transducer housing comprises a means of registering, such as a detector, configured to detect which of the mouthpieces is attached to the transducer housing. Means for registering which mouthpiece 2 is attached to the transducer housing 3 may comprise: Manual input in the sensor or transducer of the transducer housing 3 such as a selector with, e.g., three possible selections, or automatic input in the sensor or transducer of the transducer housing 3 such as an RFID tag embedded in the mouthpiece 2 and a corresponding RFID reader in the transducer housing 3.

All the figures are highly schematic and not necessarily to scale, and they show only those parts which are necessary in order to elucidate the invention, other parts being omitted or merely suggested.

Although the invention has been described in the above in connection with preferred embodiments of the invention, it will be evident for a person skilled in the art that several modifications are conceivable without departing from the invention as defined by the following claims.

The invention claimed is:

1. A medical device for monitoring a physiological pulmonary condition of a user, comprising:

at least one mouthpiece, and
a transducer housing, the at least one mouthpiece and the transducer housing being separate elements, the at least one mouthpiece being physically attachable to the transducer housing,
the at least one mouthpiece, when attached to the transducer housing, being configured to pass at least part of a flow of exhaled or inhaled air through the mouthpiece to the transducer housing,
wherein a sensor of the transducer housing is configured to measure one or more characteristics of the flow of exhaled or inhaled air passed to the transducer housing and to provide data of the flow of exhaled air passed to the transducer housing,
wherein the mouthpiece comprises a flow channel having a first orifice and a second orifice, the first orifice being configured for the user to blow exhaled air or to draw inhaled air into the mouthpiece, and the second orifice being configured for discharge from the mouthpiece or intake of the exhaled air or inhaled air,
wherein the transducer housing comprises an air passage having an inlet and an outlet, and, when the mouthpiece is attached to the transducer housing, the inlet is fluidly connected with the flow channel and the outlet is fluidly connected with the sensor of the transducer housing, said air passage being configured to pass at least part of the exhaled air or inhaled air from the flow channel to the sensor of the transducer housing,
wherein the mouthpiece further comprises a third orifice disposed in one side of the mouthpiece, and, when the mouthpiece is attached to the transducer housing, the inlet of the air passage is fluidly connected with the flow channel via the third orifice,
wherein the transducer housing comprises a pivot joint configured for pivotably attaching the mouthpiece, wherein the mouthpiece is releasable from the pivot joint, thereby enabling the mouthpiece to be detached from the transducer housing, and
wherein the air passage extends along and parallel with the pivot axis of the pivot joint.

2. The medical device according to claim 1, wherein the at least one mouthpiece and the transducer housing, when being physically attached to each other, together constitute a hand-held medical device.

3. The medical device according to claim 1, wherein the at least one mouthpiece is void of electronic elements having physical contact with an interior of the flow channel.

4. The medical device according to claim 1, wherein the mouthpiece comprises a restriction or an obstruction configured to create a pressure drop.

5. The medical device according to claim 4, wherein the restriction or obstruction is a decreasing cross-sectional area of the flow channel, and the restriction or obstruction is the cross-sectional area at the second orifice being smaller than cross-sectional area at the first orifice.

6. The medical device according to claim 4, comprising several mouthpieces, and the transducer housing comprises a detector configured to detect which of the mouthpieces is attached to the transducer housing.

7. The medical device according to claim 6, wherein the restriction or obstruction of one mouthpiece is smaller than another of the several mouthpieces.

8. The medical device according to claim 1, wherein the mouthpiece has a first position in relation to the transducer housing, in which first position the first orifice of the mouthpiece is at least partly blocked for exhalation or inhalation of air by a user through the mouthpiece to the transducer housing, the mouthpiece having a second position in relation to the transducer, in which second position the first orifice of the mouthpiece is fully open for exhalation or inhalation of air by a user through the mouthpiece to the transducer housing, and wherein said mouthpiece is attached to the transducer housing in both the first position and the second position, so that the mouthpiece and the transducer constitute a single unit, both when in use for monitoring a physiological pulmonary condition of a user and when not in use.

9. The medical device according to claim 1, wherein the mouthpiece has a first position in relation to the transducer housing, in which first position the first orifice is at least partly blocked for air to pass from the mouthpiece to the transducer housing, the mouthpiece having a second position in relation to the transducer housing, in which second position the air passage is fully open for air to pass from the mouthpiece to the transducer housing, and wherein said mouthpiece is attached to the transducer housing in both the first position and the second position, so that the mouthpiece and the transducer housing constitute a single unit, both when in use for monitoring a physiological pulmonary condition of a user and when not in such use.

10. The medical device according to claim 1, wherein the at least one mouthpiece has:
   a first status in relation to the attachment to the transducer housing, in which first status measuring the flow of exhaled air or inhaled air passed to the sensor of the transducer housing is disabled, and
   a second status in relation to the attachment to the transducer housing, in which second status measuring the flow of exhaled air or inhaled air passed to the sensor of the transducer housing is enabled.

11. The medical device according to claim 10, wherein the first status is a retracted position of the mouthpiece in relation to the transducer housing, and the second status is an extended position of the mouthpiece in relation to the transducer housing.

12. The medical device according to claim 11, wherein the mouthpiece is configured to pivot between the retracted position and the extended position.

13. The medical device according to claim 1, wherein a transmitter of the transducer housing is configured to transmit the data of the flow of exhaled air or inhaled air passed to the transducer housing further on to a remote data receiver, and the remote data receiver being located by at least one of the following recipients of the data: a hospital medicating the user, a doctor of the user, a relative of the user, the user herself or himself.

14. A method for monitoring a physiological pulmonary condition of a user of the medical device according to claim 1, comprising:
   displacing the mouthpiece from a retracted position to an extended position for measuring a flow of air exhaled or inhaled by the user and blown or drawn into the mouthpiece,
   the user blowing air into a first orifice of the mouthpiece, through a flow channel of the mouthpiece and through a second orifice of the mouthpiece,
   passing at least part of the flow of air from the flow channel of the mouthpiece to an air passage between the mouthpiece and the transducer housing,
   passing the flow of exhaled air or inhaled air from the air passage to a sensor of the transducer housing for measuring characteristics, and
   displaying data related to the characteristics of the flow of exhaled air or inhaled air, said data being displayed on the transducer housing and/or on a remote data receiver.

15. The method according to claim 14, further comprising:
   measuring and recording, by the transducer housing and/or by a remote data receiver, first data of a first exhalation or inhalation and blowing of air or drawing of air into the mouthpiece,
   measuring and recording, by the transducer housing and/or by a remote data receiver, second data of a second exhalation or inhalation and blowing of air or drawing of air into the mouthpiece,
   said first data and said second data being measured and recorded with a time interval between measuring the first data and the second data,
   measuring a possible change of data between the first data and the second data so as to establish any difference between the first data and the second data, and
   using a possible change between the first data and the second data to establish whether the physiological pulmonary condition of the user is deteriorating or improving.

16. A system for monitoring a physiological pulmonary condition of a user, comprising:
   the medical device according to claim 1,
   a data transmission channel between the medical device and a remote data receiver,
   a data recorder configured to record data received by the remote data receiver,
   the data transmission channel being at least one of the following wireless data transmission channels: WPAN, WLAN, WMAN and mobile/cellular networks, and
   the data recorder being embedded in at least one of the following remote data receivers: a mobile phone or cellular phone, a watch or other wearable, a tablet, a laptop,
   wherein the data recorder is capable of recording first data and second data, the second data being different from the first data, and are provided with displaying display configured to display the first data and the second data.

* * * * *